(12) United States Patent
Sood et al.

(10) Patent No.: US 7,560,254 B2
(45) Date of Patent: *Jul. 14, 2009

(54) ALLELE SPECIFIC PRIMER EXTENSION

(75) Inventors: Anup Sood, Flemington, NJ (US); Shiv Kumar, Belle Mead, NJ (US); Carl Fuller, Berkeley Heights, NJ (US); John Nelson, Hillsborough, NJ (US); John Macklin, Wenonah, NJ (US)

(73) Assignee: GE Healthcare Bio-Sciences Corp., Piscataway, NJ (US)

( * ) Notice: Subject to any disclaimer, the term of this patent is extended or adjusted under 35 U.S.C. 154(b) by 438 days.

This patent is subject to a terminal disclaimer.

(21) Appl. No.: 10/651,558

(22) Filed: Aug. 29, 2003

(65) Prior Publication Data

US 2004/0048301 A1 Mar. 11, 2004

Related U.S. Application Data

(63) Continuation-in-part of application No. 10/113,030, filed on Apr. 1, 2002, now Pat. No. 7,052,839, and a continuation-in-part of application No. 10/113,025, filed on Apr. 1, 2002, now Pat. No. 7,033,762.

(60) Provisional application No. 60/406,892, filed on Aug. 29, 2002, provisional application No. 60/406,893, filed on Aug. 29, 2002, provisional application No. 60/406,894, filed on Aug. 29, 2002, provisional application No. 60/315,798, filed on Aug. 29, 2001.

(51) Int. Cl.
*C12P 19/34* (2006.01)
*C12Q 1/68* (2006.01)
*C07H 21/02* (2006.01)
*C07H 21/04* (2006.01)
*C07H 21/00* (2006.01)

(52) U.S. Cl. ................... 435/91.2; 435/6; 435/91.1; 536/23.1; 536/24.3; 536/24.33; 536/25.3; 536/25.32

(58) Field of Classification Search ............... 435/6, 435/91.1, 91.2, 183; 436/94; 536/23.1, 24.3, 536/24.33, 25.3

See application file for complete search history.

(56) References Cited

U.S. PATENT DOCUMENTS

| 5,270,185 | A | | 12/1993 | Margolskee |
| 5,518,900 | A | | 5/1996 | Nikiforov et al. |
| 5,565,323 | A | * | 10/1996 | Parker et al. ................... 435/6 |
| 5,759,772 | A | | 6/1998 | Kirkpatrick et al. |
| 5,849,487 | A | | 12/1998 | Hase et al. |
| 6,001,571 | A | * | 12/1999 | Mandecki ....................... 435/6 |
| 6,187,286 | B1 | | 2/2001 | Elmaleh et al. |
| 6,255,083 | B1 | | 7/2001 | Williams |
| 6,399,355 | B1 | * | 6/2002 | Kwong et al. ............... 435/238 |
| 6,936,702 | B2 | * | 8/2005 | Williams et al. ........... 536/22.1 |
| 7,033,762 | B2 | * | 4/2006 | Nelson et al. .................. 435/6 |
| 7,041,812 | B2 | * | 5/2006 | Kumar et al. .............. 536/23.1 |
| 2002/0009716 | A1 | * | 1/2002 | Abarzua ........................ 435/5 |
| 2003/0134807 | A1 | | 7/2003 | Hardin et al. |

FOREIGN PATENT DOCUMENTS

| WO | WO 96/22297 | 7/1996 |
| WO | WO 99/16832 | 4/1999 |
| WO | WO 00/70073 | 11/2000 |
| WO | WO 01/94609 | 12/2001 |
| WO | WO 02/40126 | 5/2002 |
| WO | WO 02/44425 | 6/2002 |
| WO | WO 03/020734 | 3/2003 |
| WO | WO 03/020891 | 3/2003 |
| WO | WO 03/020984 | 3/2003 |

OTHER PUBLICATIONS

Attachment for phosphatase.*
Newton, C. R., et al. "The Production of PCR Products with 5' Single-Stranded Tails Using Primers that Incorporate Novel Phosphoramidite Intermediates" Nucleic Acid Research, Oxford University Press, Surrey, GB, vol. 21, No. 5, 1993, pp. 1155-1162.
Dyatkina, N., et al. "Modified Triphosphates of carbocyclic nucleoside analogues: synthesis, stability towards alkaline phosphatase and substrate properties for some DNA polymerases" Bioorganic and Medicinal Chemistry Letters, Oxford, GB, vol. 6, No. 22, Nov. 19, 1996, pp. 2639-2642.
Su, S-H., et al. "Novel non-nucleosidic phosphoamidites for olignucleotide modification and labeling" Bioorganic and Medicinal Chemistry Letters, Oxford, GB, vol. 7, No. 13, Jul. 8, 1997, pp. 1639-1644.
Arzumanov Andrey, A., et al. "Gamma-Phosphate-substituted 2'-deoxynucleoside 5'-triphosphates as substrates for DNA polymerases" Journal of Biological Chemistry, vol. 271, No. 40, 1996, pp. 24389-24394.

* cited by examiner

*Primary Examiner*—Frank W Lu
(74) *Attorney, Agent, or Firm*—Yonggang Ji

(57) ABSTRACT

A method of characterizing a nucleic acid sample is provided that includes the steps of: (a) conducting a DNA polymerase reaction that includes the reaction of a template, an allele specific primer, at least one terminal phosphate-labeled nucleotide, DNA polymerase, and optionally an enzyme having 3'→5' exonuclease activity when the primer is non-hydrolyzable, which reaction results in the production of labeled polyphosphate; (b) permitting the labeled polyphosphate to react with a phosphatase to produce a detectable species; (c) detecting the detectable species; and (d) characterizing the nucleic acid sample based on such detection.

19 Claims, 7 Drawing Sheets

Incorporation of all four DDAO deoxy analogs by Sequenase using matched or mismatched primer-template (A)

(B)

Matched

Mismatched ial patent

SEQUENCE LISTING

<160> NUMBER OF SEQ ID NOS: 15

<210> SEQ ID NO 1
<211> LENGTH: 19
<212> TYPE: DNA
<213> ORGANISM: artificial sequence
<220> FEATURE:
<223> OTHER INFORMATION: synthetic oligonucleotide

<400> SEQUENCE: 1
agttgctcta gcaaccatc                                                19

<210> SEQ ID NO 2
<211> LENGTH: 19

```
<212> TYPE: DNA
<213> ORGANISM: artificial sequence
<220> FEATURE:
<223> OTHER INFORMATION: synthetic oligonucleotide

<400> SEQUENCE: 2
agttgctcta gtaaccatc                                                    19

<210> SEQ ID NO 3
<211> LENGTH: 8
<212> TYPE: DNA
<213> ORGANISM: artificial sequence
<220> FEATURE:
<223> OTHER INFORMATION: synthetic oligonucleotide

<400> SEQUENCE: 3 gatggttg                                                                 8

<210> SEQ ID NO 4
<211> LENGTH: 12
<212> TYPE: DNA
<213> ORGANISM: artificial sequence
<220> FEATURE:
<223> OTHER INFORMATION: synthetic oligonucleotide

<400> SEQUENCE: 4
gatggttgct ag                                                           12

<210> SEQ ID NO 5
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 5
gatctagcaa ccatcagtac                                                   20

<210> SEQ ID NO 6
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 6
gatctagtaa ccatcagtac                                                   20

<210> SEQ ID NO 7
<211> LENGTH: 8
<212> TYPE: DNA
<213> ORGANISM: artificial sequence
<220> FEATURE:
<223> OTHER INFORMATION: synthetic oligonucleotide

<400> SEQUENCE: 7 gatggttg                                                                 8

<210> SEQ ID NO 8
<211> LENGTH: 12
<212> TYPE: DNA
<213> ORGANISM: artificial sequence
<220> FEATURE:
<223> OTHER INFORMATION: synthetic oligonucleotide

<400> SEQUENCE: 8
```

```
gatggttgct ag                                                         12

<210> SEQ ID NO 9
<211> LENGTH: 21
<212> TYPE: DNA
<213> ORGANISM: artificial sequence
<220> FEATURE:
<223> OTHER INFORMATION: synthetic oligonucleotide

<400> SEQUENCE: 9
gttctcggca tcaccatccg t                                               21

<210> SEQ ID NO 10
<211> LENGTH: 21
<212> TYPE: DNA
<213> ORGANISM: artificial sequence
<220> FEATURE:
<223> OTHER INFORMATION: synthetic oligonucleotide

<400> SEQUENCE: 10
gttctcggca tcaccatgcg t                                               21

<210> SEQ ID NO 11
<211> LENGTH: 21
<212> TYPE: DNA
<213> ORGANISM: artificial sequence
<220> FEATURE:
<223> OTHER INFORMATION: synthetic oligonucleotide

<400> SEQUENCE: 11
gttctcggca tcaccatcgg t                                               21

<210> SEQ ID NO 12
<211> LENGTH: 40
<212> TYPE: DNA
<213> ORGANISM: artificial sequence
<220> FEATURE:
<223> OTHER INFORMATION: synthetic oligonucleotide

<400> SEQUENCE: 12 caccccttatc tggttgtcga cggatggtga tgccgagaac                          40

<210> SEQ ID NO 13
<211> LENGTH: 40
<212> TYPE: DNA
<213> ORGANISM: artificial sequence
<220> FEATURE:
<223> OTHER INFORMATION: synthetic oligonucleotide

<400> SEQUENCE: 13 caccccttatc tggttgtcgg cggatggtga tgccgagaac                          40

<210> SEQ ID NO 14
<211> LENGTH: 40
<212> TYPE: DNA
<213> ORGANISM: artificial sequence
<220> FEATURE:
<223> OTHER INFORMATION: synthetic oligonucleotide

<400> SEQUENCE: 14 caccccttatc tggttgtcgc cggatggtga tgccgagaac                          40

<210> SEQ ID NO 15
<211> LENGTH: 40
<212> TYPE: DNA
<213> ORGANISM: artificial sequence
```

```
<220> FEATURE:
<223> OTHER INFORMATION: synthetic oligonucleotide

<400> SEQUENCE: 15
cacccttatc tggttgtcgt cggatggtga tgccgagaac                    40
```

ALLELE SPECIFIC PRIMER EXTENSION

CROSS REFERENCE TO RELATED APPLICATIONS

This application claims priority to U.S. provisional patent application Nos. 60/406,892, 60/406,893, and 60/406,894 all filed on Aug. 29, 2002 and to U.S. patent application Ser. No. 10/230,576 filed on Aug. 29, 2002, now U.S. Pat. No. 7,041,812 B2, and to U.S. patent application Ser. No. 10/358,818 filed on Feb. 5, 2003, now U.S. Pat. No. 7,223,541 B2. This application is a continuation-in-part of U.S. patent application Ser. Nos. 10/113,030 and 10/113,025 both filed on Apr. 1, 2002, now U.S. Pat. Nos. 7,052,839 B2 and 7,033,762 B2. All above applications claim the benefit of U.S. provisional patent application No. 60/315,798 filed on Aug. 29, 2001. The disclosures of U.S. provisional patent application No. 60/315,798 are incorporated herein by reference in their entireties.

FIELD OF INVENTION

The present invention relates generally to methods of detecting and characterizing a polynucleotide in a sample, based on the use of a normal or non-hydrolyzable primer and terminal-phosphate-labeled nucleotides as substrates for DNA polymerase. The invention further relates to a method of detecting a polymorphism of a specific nucleotide base in a target polynucleotide. The labels employed are enzyme-activatable and include chemiluminescent, fluorescent, electrochemical and chromophoric moieties as well as mass-tags.

BACKGROUND OF INVENTION

Methods are known for detecting specific nucleic acids or analytes in a sample with high specificity and sensitivity. A method of analysis that is based on the complimentarily between nucleotide sequences allows for the direct analysis of genetic characters. This provides a very useful means for identifying genetic disorders or a carcinomatous change of normal cells.

However, detection and characterization of a trace amount of a target nucleotide in a sample is difficult. Therefore, methods for direct detection of the gene generally require first amplifying a nucleic acid sequence based on the presence of a specific target sequence or analyte. Following amplification, the amplified sequences are detected and quantified. Conventional detection systems for nucleic acids include detection of fluorescent labels, fluorescent enzyme-linked detection systems, antibody-mediated label detection, and detection of radioactive labels.

As a method of amplifying a nucleic acid sequence, the PCR (polymerase chain reaction) process is known. Presently, the PCR is the most conventional means for in vitro amplification of nucleic acid. However, the PCR has certain disadvantages, including the requirement for strict temperature control, inadequate quantification due to logarithmic amplification, and the danger of erroneous results brought about by simultaneous amplification of trace amounts of contaminated DNA.

In addition to amplification methods which involve detection and quantification of the sequences, there are signal amplification methods which detect amplified decomposition products, i.e., a product or by-product of a reaction is amplified as the signal from a target nucleic acid.

For example, a cycling assay has been developed which utilizes λ-exonuclease to specifically cleave double stranded DNA (C. G. Copley et al., Bio Techniques, Vol. 13, No. 6, pp 882-892, 1992). This method involves hybridizing an oligonucleotide probe with a nucleic acid sequence complimentary thereto, allowing λ-exonuclease to act on the formed double-stranded DNA to decompose the hybridized probe. The probe is replaced by another probe, which is then decomposed. In this way, a cycling reaction repeats. In this method, the presence of a target DNA sequence is estimated by the detection of the decomposed probe. A disadvantage of this method is that the λ-exonuclease requires a probe, which is phosphorylated at its 5'-terminal as the substrate. Following chemical synthesis of the probe by known methods, the 5'-terminal needs to be phosphorylated, and it is often difficult to confirm that all 5'-terminals are phosphorylated completely. An additional problem of this method is the low turnover number of cycling reactions, i.e., the number of times hybridization between the primer and target nucleotide occurs. The turnover number is low since the hybridization step must repeatedly occur.

An additional cycling assay by an exonuclease has been disclosed in EP 500224/A1. In this method, the synthesis of a DNA strand complimentary to a target DNA proceeds from a primer simultaneously with the decomposition of the same primer from the other side by a 5'→3' exonuclease such that another primer hybridizes with the target sequence in place of the decomposed primer hybridized before. Therefore, in a single cycle reaction both the synthesis of a complimentary strand by DNA polymerase as well as the degradation of the synthesized strand repeatedly occurs. A disadvantage of this method is the low turnover number, with the hybridization step being rate limiting in that it must repeatedly occur.

A further cycling assay for detection of a polynucleotide containing a specific sequence is disclosed in U.S. Pat. No. 5,849,487. This method relies on signal amplification and detection of decomposition products. This method includes using a combination of nucleic acid polymerase, 3'→5' exonuclease, a nuclease-resistant primer, a target nucleic acid, which may be DNA at limiting concentration, and at least one deoxynucleoside triphosphate (dNTP) to detect the target nucleic acid sequence. The method further includes synthesizing a complimentary strand being a nucleotide species located adjacent to the 3'-terminal of the nuclease-resistant primer, followed by decomposition of the nucleotide species joined to the end of the primer and detection of the resulting pyrophosphoric acid or deoxynucleoside monophosphate, the synthesis and decomposition of the nucleotide species being repeated one or more times. A disadvantage of this method as well as other detection methods presently widely in use is the need to separate labeled starting material from a final labeled product or by-product. Such separations generally require gel electrophoresis or immobilization of a target nucleic acid sequence onto a membrane for detection. For example, in U.S. Pat. No. 5,849,487, the deoxynucleoside monophosphate formed by a nuclease reaction is separated by chromotography and optically measured. Alternatively, the pyrophosphoric acid which is formed upon incorporation of a complimentary base by DNA polymerase may be allowed to react with adenosine-5'-phosphosulfate and adenosine triphosphate sulfurase to form adenosine triphosphate, which is then detected using a luciferin-luciferase reaction; this presents the disadvantage of requiring additional reagents and incubation steps.

Moreover, U.S. Pat. No. 5,849,487 uses only the presence or absence of a nucleotide species remaining after nuclease digestion to detect a mutation of a specific nucleotide base in the target. That is to say, the nucleotide will join onto the 3' end of the primer only if a specific base is, or is not, the mutation to be detected. The patent fails to disclose a method to identify the actual mutation present by first analysis.

Another signal amplification method for the detection of specific polynucleotide sequence is based on an allele specific primer extension reaction and generation of multiple molecules of pyrophosphate per molecule of target template (G-H Zhou et. al., Nucleic Acids Research 2001, 29(19), e93). The method relies on discriminatory extension of a perfectly matched primer over a 3'-base mismatched primer (C. R. Newton et. al., Nucleic Acids Research 1989, 17(7), 2503) and detection of pyrophosphate by conversion to ATP as described above. The discrimination between 3'-end matched and mismatched primer extension can be further increased by providing a fixed mismatch in the primers 2 or 3 bases from the 3' end. Signal is amplified by the polymerization of several nucleotides, extending the primer as shown in FIG. 1 and producing several molecules of labelled pyrophosphate for each primer extended. A major problem with this method is the contaminating pyrophosphate that is generally present in the dNTP samples and can cause high background. It can be removed by careful purification of nucleotides or using pyrophosphatase cleanup of nucleotides prior to use. Both of these methods are labor intensive. Further, depending upon the temperature used for assay, degradation of dNTP, forming pyrophosphate, can interfere. For this reason, this method can not be reliably used at high temperature or in a thermal cycling process to amplify signal.

It has been known that DNA and RNA polymerases are able to recognize and utilize nucleosides with a modification at or in place of the gamma position of the triphosphate moiety. It is further known that the ability of various polymerases to recognize and utilize gamma-modified nucleoside triphosphates appears to vary depending on the moiety attached to the gamma phosphate.

A colorimetric assay for monitoring RNA synthesis from RNA polymerases in the presence of a gamma-phosphate modified nucleotide has been reported (Ref. Vassiliou W, Epp J B, Wang B B, Del Vecchio A M, Widlanski T, Kao C C. Exploiting polymerase promiscuity: A simple colorimetric RNA polymerase assay. Virology. 2000 Sep. 1; 274(2):429-37; C. C. Kao et. al, U.S. Pat. No. 6,399,335). In these reports, RNA polymerase reactions were performed in the presence of a gamma-modified, alkaline phosphatase resistant nucleoside triphosphate which was modified at its gamma phosphate with a dinitrophenyl group. When RNA polymerase reactions were performed in the presence of this gamma-modified NTP as the sole nucleoside triphosphate and a homopolymeric template, it was found that RNA polymerase could recognize and utilize the modified NTP. Moreover, when the polymerase reactions were performed in the presence of an alkaline phosphatase, which digested the p-nitrophenyl pyrophosphate aldo-product of a phosphoryl transfer to the chromogenic p-nitrophenylate, an increase in absorbance was reported. This report, however, only describes a way to quantify polymerase activity and does not show a way to identifying a polynucleotide sequence in presence of other polynucleotide sequences.

It would, therefore, be of benefit to provide methods of detecting and characterizing a nucleic acid, which methods would include utilization of terminal-phosphate-labeled nucleotides as substrates for DNA polymerase in a signal amplification protocol. It would further be of benefit if such methods would employ enzyme-activatable labels at the terminal phosphate of the nucleotide for production of an amplified detectable species from a target nucleic acid which would eliminate the need to separate labeled starting materials from labeled products or by-products. Moreover, it would be highly desirable if such methods for detecting and characterizing nucleic acids would allow for real-time monitoring of a heteropolymeric target nucleic acid using routine lab instrumentation.

SUMMARY OF INVENTION

An aspect of the present invention is to provide a homogenous method of detecting and characterizing a polynucleotide sequence in which terminal phosphate modified dNTP's are used in conjunction with a polymerase, a phosphatase and allele specific primers to generate an amplified signal which can be detected without separation of reaction components.

The present invention provides methods for detecting a nucleic acid sample. One method includes the steps of: (a) conducting a DNA polymerase reaction, the reaction including the reaction of a template, a primer, at least one terminal phosphate-labeled nucleotide and a DNA polymerase, which reaction results in the production of labeled polyphosphate; (b) permitting the labeled polyphosphate to react with a phosphatase to produce a detectable species; and (c) detecting the detectable species.

Further provided is a method of detecting a nucleic acid sample including the steps of: (a) conducting a DNA polymerase reaction, the reaction comprising the reaction of a template, a primer, at least one terminal phosphate-labeled nucleotide having 4 or more phosphate groups in the polyphosphate chain and a DNA polymerase, which reaction results in the production of labeled polyphosphate; and (b) detecting the labeled polyphosphate.

Another aspect of the invention relates to a method of detecting a nucleic acid sample comprising the steps of: (a) conducting a DNA polymerase reaction, the reaction comprising the reaction of a template, a primer, at least one terminal phosphate-labeled nucleotide having 4 or more phosphate groups in the polyphosphate chain and a DNA polymerase, which reaction results in the production of labeled polyphosphate; (b) permitting the labeled polyphosphate to react with a phosphatase to produce a detectable species; and (c) detecting the detectable species.

The invention further provides methods of characterizing a nucleic acid sample. For example, the invention provides a method including the steps of: (a) conducting a DNA polymerase reaction, the reaction including the reaction of a template, a primer, at least one terminal phosphate-labeled nucleotide and a DNA polymerase, which reaction results in the production of labeled polyphosphate; (b) permitting the labeled polyphosphate to react with a phosphatase to produce a detectable species; (c) detecting the detectable species; and (d) characterizing the nucleic acid based on the detection.

Further encompassed by the invention is a method of characterizing a nucleic acid sample including the steps of: (a) conducting a DNA polymerase reaction, the reaction comprising the reaction of a template, a primer, at least one terminal phosphate-labeled nucleotide having 4 or more phosphate groups in the polyphosphate chain and a DNA polymerase, which reaction results in the production of labeled polyphosphate; (b) detecting said labeled polyphosphate; and (c) characterizing the nucleic acid sample based on the detection.

Also provided is a method of characterizing a nucleic acid sample including the steps of: (a) conducting a DNA polymerase reaction, the reaction comprising the reaction of a template, a primer, at least one terminal phosphate-labeled nucleotide having 4 or more phosphate groups in the polyphosphate chain and a DNA polymerase, which reaction results in the production of labeled polyphosphate; (b) permitting the labeled polyphosphate to react with a phosphatase to produce a detectable species having a signal profile characteristic of the sample; (c) detecting the detectable species; and (d) characterizing the nucleic acid sample based on the signal profile.

Moreover, the present invention provides methods of detecting a polymorphism of a specific nucleotide base in a target nucleic chain. One inventive method includes the steps of: (a) conducting a DNA polymerase reaction, the reaction including the reaction of a template, an allele specific primer, at least one terminal phosphate-labeled nucleotide and a DNA polymerase, which reaction results in the production of labeled polyphosphate; (b) permitting the labeled polyphosphate to react with a phosphatase to produce a detectable species; (c) detecting the detectable species; and (d) characterizing the polymorphism in the nucleic acid sequence based on the presence or absence of the detectable species.

Additionally provided is a method of detecting a polymorphism of a specific nucleotide base in a target nucleic acid sequence which includes the following steps: (a) conducting a DNA polymerase reaction, the reaction comprising the reaction of a template, an allele specific primer, at least one terminal phosphate-labeled nucleotide having 4 or more phosphate groups in the polyphosphate chain and a DNA polymerase, which reaction results in the production of labeled polyphosphate if the 3'-terminal base of the primer is base-paired with the corresponding template base; (b) detecting the labeled polyphosphate; and (c) characterizing the polymorphism in the nucleic acid sequence based on the presence or absence of the labeled polyphosphate.

Further encompassed by the invention is a method of detecting a polymorphism of a specific nucleotide base in a target nucleic acid sequence including the steps of: (a) conducting a DNA polymerase reaction, the reaction comprising the reaction of a template, an allele specific primer, at least one terminal phosphate-labeled nucleotide having 4 or more phosphate groups in the polyphosphate chain and a DNA polymerase, which reaction results in the production of labeled polyphosphate if the 3'-terminal base of the primer is base-paired with the corresponding template base; (b) permitting the labeled polyphosphate to react with a phosphatase to produce a detectable species; (c) detecting the detectable species; and (d) characterizing the polymorphism in the nucleic acid sequence based on the presence or absence of the detectable species.

Moreover, the present invention provides methods of detecting a polymorphism of a specific nucleotide base in a target nucleic acid chain. One such method includes the steps of: (a) conducting a DNA polymerase reaction, the reaction including the reaction of a template, an allele specific non-hydrolyzable primer, at least one terminal phosphate-labeled deoxynucleotide, a DNA polymerase and an enzyme having 3'→5' exonuclease activity, wherein the enzyme may be selected from DNA polymerases, exonucleases and combinations thereof, which reaction results in the production of labeled polyphosphate; (b) permitting the labeled polyphosphate to react with a phosphatase to produce a detectable species; (c) detecting the detectable species; and (d) characterizing the polymorphism in the nucleic acid sequence based on the presence or absence of the detectable species.

Further encompassed by the invention is a method of detecting a polymorphism of a specific nucleotide base in a target nucleic acid sequence including the steps of: (a) conducting a DNA polymerase reaction, the reaction comprising the reaction of a template, an allele specific non-hydrolyzable primer, at least one terminal phosphate-labeled deoxynucleotide having 4 or more phosphate groups in the polyphosphate chain, a DNA polymerase and an enzyme having 3'→5' exonuclease activity, wherein the enzyme may be selected from the group consisting of DNA polymerases, exonucleases and combinations thereof, which reaction results in the production of labeled polyphosphate if the 3'-terminal base of the primer is base-paired with the corresponding template base; (b) detecting the labelled polyphosphate; and (c) characterizing the polymorphism in the nucleic acid sequence based on the presence or absence of the labelled polyphosphate.

Further encompassed by the invention is a method of detecting a polymorphism of a specific nucleotide base in a target nucleic acid sequence including the steps of: (a) conducting a DNA polymerase reaction, the reaction comprising the reaction of a template, an allele specific non-hydrolyzable primer, at least one terminal phosphate-labeled deoxynucleotide having 4 or more phosphate groups in the polyphosphate chain, a DNA polymerase and an enzyme having 5'→3' exonuclease activity, wherein the enzyme may be selected from the group consisting of DNA polymerases, exonucleases and combinations thereof, which reaction results in the production of labeled polyphosphate if the 3'-terminal base of the primer is base-paired with the corresponding template base; (b) permitting the labeled polyphosphate to react with a phosphatase to produce a detectable species; (c) detecting the detectable species; and (d) characterizing the polymorphism in the nucleic acid sequence based on the presence or absence of the detectable species.

Kits for detecting a polynucleotide are further provided by the invention, one kit includes: (a) at least one terminal-phosphate-labeled nucleotide; (b) a DNA polymerase; and (c) a phosphatase.

Kits for detecting a polynucleotide are further provided by the invention, one kit includes: (a) at least one terminal-phosphate-labeled nucleotide; (b) a DNA polymerase; (c) a phosphatase; and (d) a nuclease with enzymatic activity sufficient to decompose DNA in the 3'→5' direction.

A further kit for detection of a polynucleotide is provided which includes: (a) at least one terminal-phosphate-labeled nucleotide; (b) a phosphatase; and (c) a DNA polymerase with enzymatic activity sufficient to decompose DNA in the 3'→5' direction.

A further aspect of the present invention is to provide a kit for the detection of a polymorphism of a specific nucleotide base in a target nucleic acid chain, one kit including: (a) at least one terminal-phosphate-labeled nucleotide; (b) a DNA polymerase; and (c) and a phosphatase.

A further aspect of the present invention is to provide a kit for the detection of a polymorphism of a specific nucleotide base in a target nucleic acid chain, one kit includes: (a) at least one terminal-phosphate-labeled nucleotide; (b) a DNA polymerase; (c) a phosphatase; and (d) a nuclease with enzymatic activity sufficient to decompose DNA in the 3'→5' direction.

Lastly, a kit is provided herein for the detection of a polymorphism of a specific nucleotide base in a target nucleic acid chain that includes: (a) at least one terminal-phosphate-labeled nucleotide; (b) a phosphatase; and (c) a DNA polymerase with enzymatic activity sufficient to decompose DNA in a 3'→5' direction.

DETAILED DESCRIPTION OF INVENTION

Figure 1:
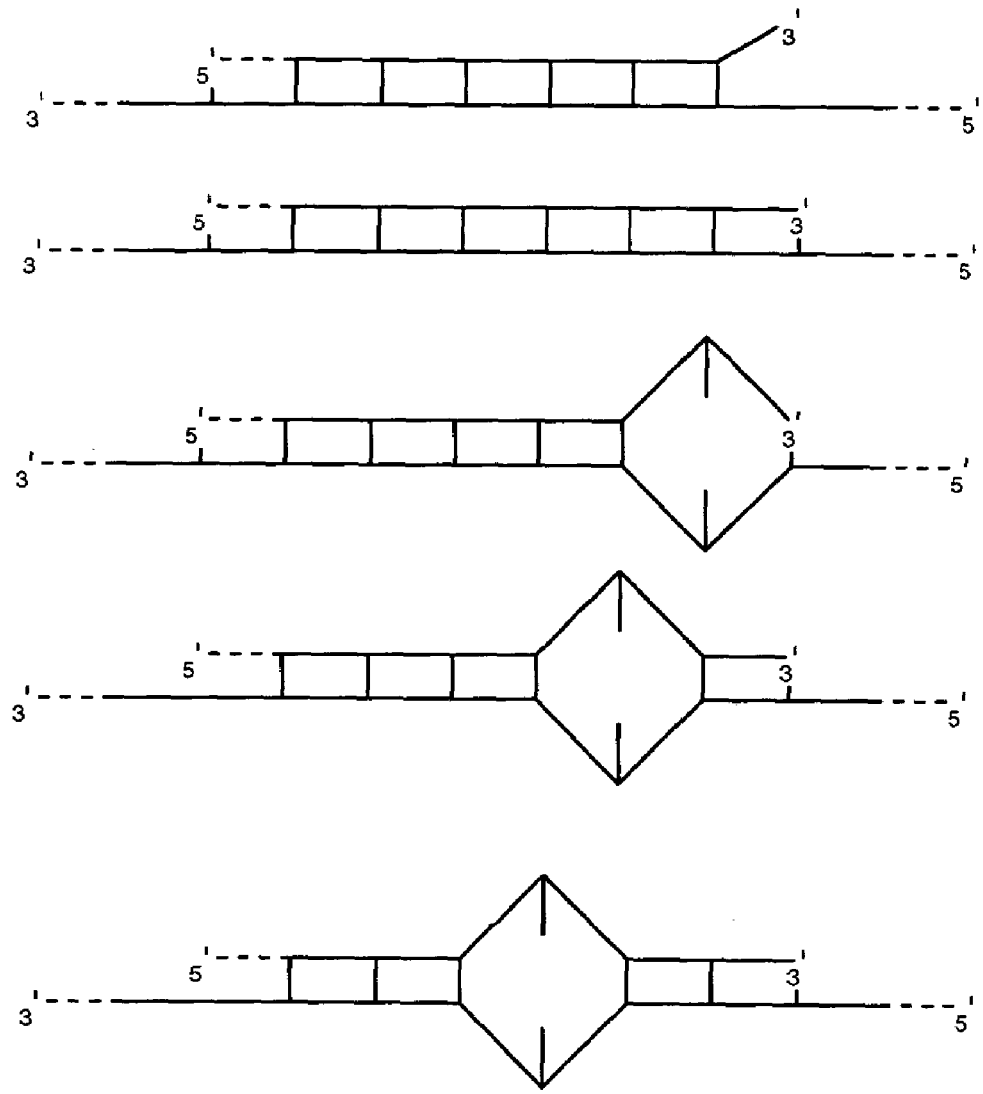
FIG. 1 is a cartoon representation of allele specific primers useful in the current invention upon base-pairing with template. Vertical lines connecting both horizontal lines represent matched base pairs.

The term "nucleoside" as defined herein is a compound including a purine deazapurine, or pyrimidine base linked to a sugar or a sugar substitute, such as a carbocyclic or acyclic linker at the 1' position or equivalent position and includes 2'-deoxy and 2'-hydroxyl, 2',3'-dideoxy forms, as well as other substitutions.

The term "nucleotide" as used herein refers to a phosphate ester of a nucleoside, wherein the esterification site typically corresponds to the hydroxyl group attached to the C-5 position of the pentose sugar.

The term "allele specific primer" referred herein is a primer whose 3'-terminal base is complementary to the corresponding template base for a particular allele at a polymorphic site.

The terms "matched primer" or "mismatched primer" as used herein only refers to the complementarity of the 3'-terminal base of the primer to the corresponding template base. Matched primer is a primer where the 3'-terminal base is complementary to the corresponding template base and mismatched primer is a primer where the 3'-terminal base is non-complementary to the corresponding template base.

The term "oligonucleotide" includes linear oligomers of nucleotides or derivatives thereof, including deoxyribonucleosides, ribonucleosides, and the like. Throughout the specification, whenever an oligonucleotide is represented by a sequence of letters, the nucleotides are in the 5'→3' order from left to right where A denotes deoxyadenosine, C denotes deoxycytidine, G denotes deoxyguanosine, and T denotes thymidine, unless noted otherwise.

The term "primer" refers to a linear oligonucleotide that anneals in a specific way to a unique nucleic acid sequence.

The phrase "target nucleic acid sequence" or "nucleic acid template" and the like refers to a nucleic acid whose sequence identity, or ordering or location of nucleosides is determined by one or more of the methods of the present invention.

The present invention relates to methods of detecting and characterizing the polynucleotide in a sample wherein a convenient assay is used for monitoring the addition of terminal-phosphate-labeled nucleotides to the 3'-terminus of a 3'-end matched primer. DNA polymerases synthesize oligonucleotides via transfer of a nucleoside monophosphate from a deoxynucleoside triphosphate (dNTP) to the 3' hydroxyl of a growing oligonucleotide chain.

The force which drives this reaction is the cleavage of an anhydride bond and the con-commitant formation of an inorganic pyrophosphate. The present invention utilizes the finding that structural modification of the terminal-phosphate of the nucleotide does not abolish its ability to function in the polymerase reaction. The oligonucleotide synthesis reaction involves direct changes only at the α- and β-phosphoryl groups of the nucleotide, allowing nucleotides with modifications at the terminal phosphate position to be valuable as substrates for nucleic acid polymerase reactions.

The methods provided by this invention utilize a nucleoside polyphosphate analogue, such as a deoxynucleoside polyphosphate or dideoxynucleoside polyphosphate analogue with an electrochemical label, mass tag, or a chromogenic, chemiluminescent, or fluorescent dye label attached to the terminal-phosphate. When a nucleic acid polymerase uses this analogue as a substrate, an enzyme-activatable label is present on the inorganic polyphosphate by-product of phosphoryl transfer. Cleavage of the polyphosphate product of phosphoryl transfer by a phosphatase, results in a detectable change in the label attached thereon. For example, if 3-cyanoumbelliferone dye is attached via its hydroxyl group to the terminal phosphate position of a nucleotide, the dye is not fluorescent when excited at 408 nm and it is not a substrate for alkaline phosphatase. Once this nucleotide is incorporated into DNA, the released dye inorganic polyphosphate (which also is not fluorescent when excited at 408 nm) is a substrate for alkaline phosphatase. Once de-phosphorylated, the dye becomes fluorescent when excited at 408 nm and hence detectable. The specific analysis of the polyphosphate product can be carried out in the same reaction solution as, the polymerase reactions, with no need to separate reaction products from starting materials. This allows for the detection and, optionally, quantitation of nucleic acids formed during polymerase reactions using routine instrumentation such as fluorimeters or spectrophotometers.

It is noted that while RNA and DNA polymerases are able to recognize nucleotides with modified terminal phosphoryl groups, the inventors have determined that this starting material is not a substrate for phosphatases. The scheme below shows relevant molecules in the method of this invention; namely the terminal-phosphate-labeled nucleotide, the labeled polyphosphate by-product and the enzyme-activated label.

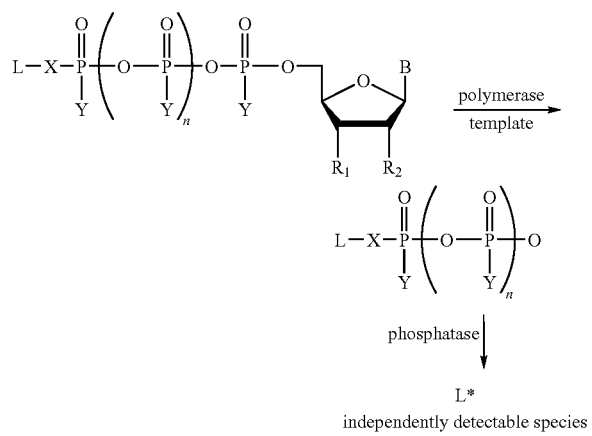

In the scheme above, n is 1 or greater, $R_1$ and $R_2$ are independently H, SH, SR, F, Br, Cl, I, $N_3$, $NH_2$, NHR, OR or OH; B is a natural or modified nucleoside base; X is O, S, or NH; Y is O, S, or $BH_3$ and L is a phosphatase activatable label which may be a chromogenic, fluorogenic, or chemiluminescent molecule, mass tag or electrochemically detectable moiety. A mass tag is a small molecular weight moiety suitable for mass spectrometry that is readily distinguishable from other reaction products due to difference in mass. An electrochemical tag is an easily oxidizable or reducible species. It has been discovered that when n is 2 or greater, the nucleotides are significantly better substrates for polymerases than when n is 1. Therefore, in preferred embodiments of the present invention, n is 2, 3 or 4. In further desired embodiments of the present invention, X and Y are O; and $R_1$ and $R_2$ are independently H or OH; B is a nucleotide base and L is a label which may be a chromogenic, fluorogenic or a chemiluminescent molecule.

In one embodiment of the method of detecting a nucleic acid sequence provided herein, the steps include conducting a DNA polymerase reaction, the reaction including the reaction of a template, a primer, at least one terminal phosphate-labeled nucleotide, a DNA polymerase, which reaction results in the production of labeled polyphosphate provided the 3'-terminal base of the primer is base-paired with the corresponding template base; permitting the labeled polyphosphate to react with a phosphatase, such as alkaline phosphatase, to produce a detectable species; and detecting the detectable species.

In the methods of characterizing nucleic acid sample provided by this invention, the target nucleic acid may be characterized by determining the presence or absence of the detectable species. Moreover, the detectable species may have a characteristic staining profile or signal profile associated with it, the profile being characteristic of the sample. This allows for characterization of the nucleic acid target based on the unique profile of the detectable species.

One particular characterization of a target nucleic acid may include the detection of a polymorphism of a specific nucleotide base in a target nucleic acid sequence. A method of detecting a polymorphism provided herein includes the steps of: (a) conducting a DNA polymerase reaction, the reaction including the reaction of a template, an allele specific primer, at least one terminal phosphate-labeled nucleotide and a DNA polymerase, which reaction results in the production of labeled polyphosphate; (b) permitting the labeled polyphosphate to react with a phosphatase to produce a detectable species; (c) detecting the detectable species; and (d) characterizing the polymorphism in the nucleic acid sequence based on the presence or absence of the detectable species.

Figure 2:
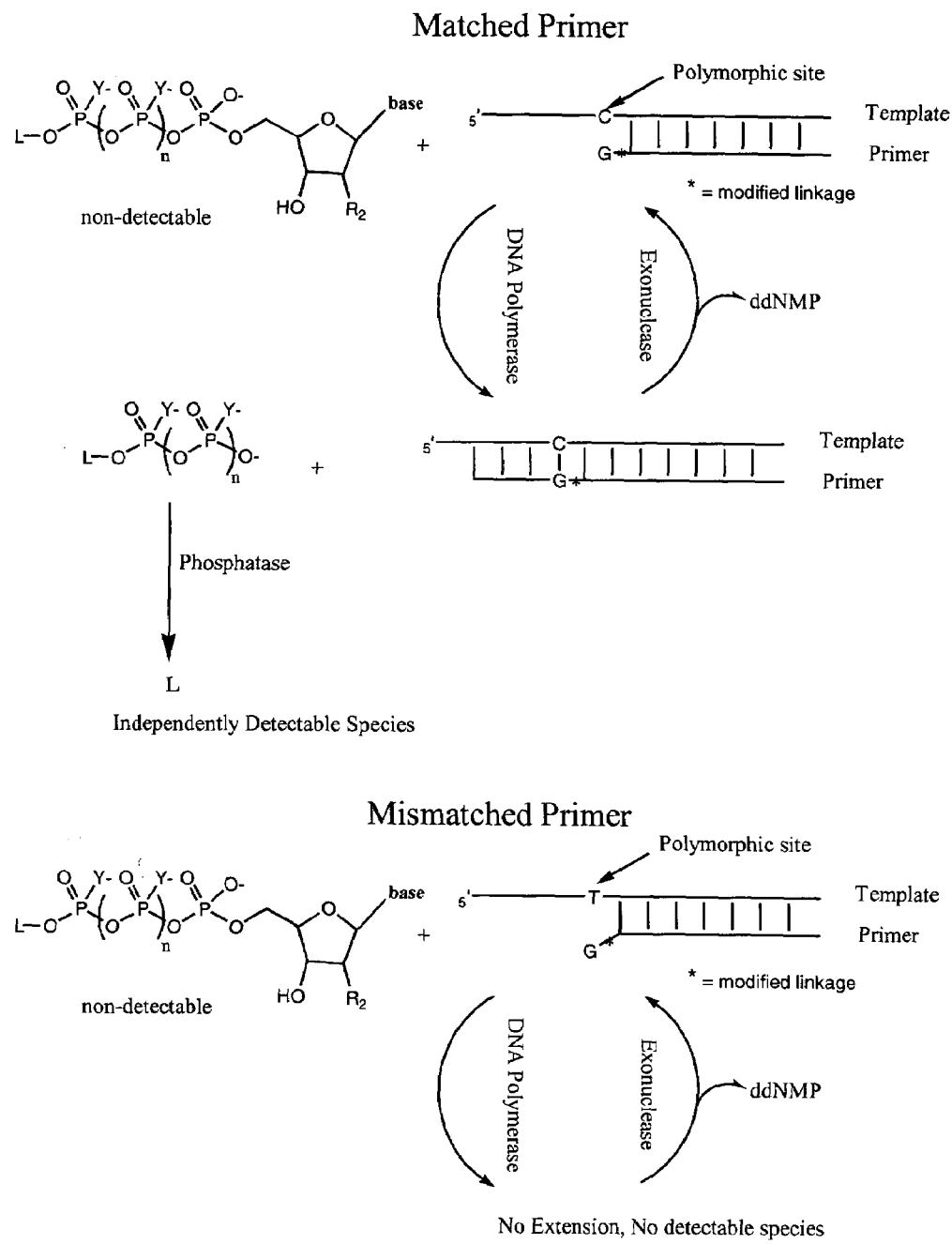
FIG. 2 shows an embodiment of a method of the present invention where terminal-phosphate-labeled nucleotides complimentary in sequence to a target polynucleotide are joined in a sequence specific manner to the 3' end of a matched non-hydrolyzable primer followed by cleavage of newly added nucleotides by 3'-exonuclease digestion, as well as generation of labeled species after hydrolysis of phosphate groups from labeled polyphosphates. The 3'-end mismatched primer is not extended.

FIG. 2 shows the general scheme employed for each of the methods described above. In this scheme, n is 1 or greater, $R_2$ is independently H, OH, SH, SR, F, Cl, Br, I, $N_3$, $NH_2$ or OR; G is guanine, or representative of a natural or modified nucleoside base; C is cytosine or representative of the base complimentary to the added nucleotide; Y is O, S, or $BH_3$ and L is a chromogenic, fluorogenic, chemiluminescent, or electrochemical label or mass tag which preferably becomes independently detectable when the phosphate is removed. As shown in FIG. 1, a target polynucleotide is hybridized with an allele specific primer having a sequence complementary at least in part to the target polynucleotide. The DNA polymerase reaction is conducted in the presence of the formed hybrid and at least one terminal-phosphate-labeled nucleotide under conditions to cause a nucleoside monophosphate derived from the terminal-phosphate-labeled nucleotide to join to the 3'-terminal end of the primer if it is complementary to the target polynucleotide. This is accompanied by the concomitant formation of a labeled product which may not be independently detectable. The labeled polyphosphate concomitantly formed during incorporation of the nucleotide species is permitted to react with a phosphatase to produce an independently detectable species, which serves as the signal from the target polynucleotide. Addition of multiple nucleotides in succession to the 3'-end generates multiple labels, which may be same or different for each of the 4 bases.

In the methods described above, the polymerase reaction may be conducted in the presence of a phosphatase, such as alkaline phosphatase, which converts the labeled polyphosphate product to the detectable label. As such, convenient assays are established for detecting and characterizing a nucleic acid that allows for continuous, real-time monitoring of detectable species formation. This represents a homogeneous assay format in that it can be performed in a single tube.

It is noted that in embodiments including terminal phosphate-labeled nucleotides having four or more phosphates in the polyphosphate chain, it is within the contemplation of the present invention that the labeled polyphosphate by-product of phosphoryl transfer may be detected without the use of phosphatase treatment. For example, it is known that natural or modified nucleoside bases, particularly guanine, can cause quenching of fluorescent markers. Therefore, in a terminal phosphate labeled nucleotide, the label may be partially quenched by the base. Upon incorporation of the nucleoside monophosphate, the labeled polyphosphate by-product may be detected due to its enhanced fluorescence. Alternatively, it is possible to physically separate the labeled polyphosphate product by chromatographic separation methods before identification by fluorescence, color, chemiluminescence, or electrochemical detection. In addition, mass spectrometry could be used to detect the products by mass difference.

The detectable species may be produced in amounts substantially proportional to the amount of target nucleic acid and, as such, is a signal for the amount of the target nucleic acid. The methods herein described may further include the step of quantifying the target nucleic acid based on the amount of detectable species produced during the reaction. The step of quantifying the target nucleic acid sequence is desired to be done by comparison of spectra produced by the detectable species with known target quantities.

In the present invention, once hybridized, the oligonucleotide primer can repeatedly function so as to permit the reaction to proceed quantitatively in an at least equal molar amount relative to the template nucleotide sequence. The amount of the oligonucleotide primer useful in the methods of the present invention should be that sufficient to attain a favorable hybridization. In general, a sensitive assay can be attained by the presence of a primer which is at least equal molar and desirably in a 5-fold excess relative to the intended range of detection.

The methods provided by the present invention may further include the step of including one or more additional detection agents in the DNA polymerase reaction. The additional detection agent may be capable of a response which is detectably different from the detectable species. For example, the additional detection agent may be an antibody.

The target nucleic acid of the present invention includes, but is not limited to, chromosomal DNA, RNA, mRNA, virus or mRNA-derived cDNA, or a natural oligonucleotide.

The methods of the present invention generally require a knowledge of the target nucleic acid sequence in the region of interest. For example, the region of interest may be that region suspected to contain a point mutation. A minimization of contamination from nucleic acid sequences other than the known target sequence is desired for amplification in the present invention.

The terminal-phosphate-labeled nucleotide useful in the methods and kits of the present invention may be represented by Formula I:

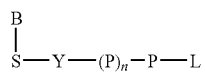

wherein P is phosphate ($PO_3$) and derivatives thereof, n is 2 or greater; Y is an oxygen or sulfur atom; B is a nitrogen-containing heterocyclic base; S is an acyclic moiety, carbocyclic moiety or sugar moiety; L is an enzyme-activatable label containing a hydroxyl group, a sulfhydryl group or an amino group suitable for forming a phosphate ester, a thioester or a phosphoramidate linkage at the terminal phosphate of a natural or modified nucleotide; P-L is a phosphorylated label which preferably becomes independently detectable when the phosphate is removed.

For purposes of the methods of the present invention, useful carbocyclic moieties have been described by Ferraro, M. and Gotor, V. in Chem Rev. 2000, volume 100, 4319-48. Suitable sugar moieties are described by Joeng, L. S. et al., in J Med. Chem. 1993, vol. 356, 2627-38; by Kim H. O. et al., in J Med. Chem. 193, vol. 36, 30-7; and by Eschenmosser A., in Science 1999, vol. 284, 2118-2124. Moreover, useful acyclic moieties have been described by Martinez, C. I., et al., in Nucleic Acids Research 1999, vol. 27, 1271-1274; by Martinez, C. I., et al., in Bioorganic & Medicinal Chemistry Letters 1997, vol. 7, 3013-3016; and in U.S. Pat. No. 5,558,91 to Trainer, G. L. Structures for these moieties are shown below, where for all moieties R may be H, OH, NHR, lower alkyl and aryl; for the sugar moieties X and Y are independently O, S, or NH; and for the acyclic moieties, X=O, S, NH, NR.

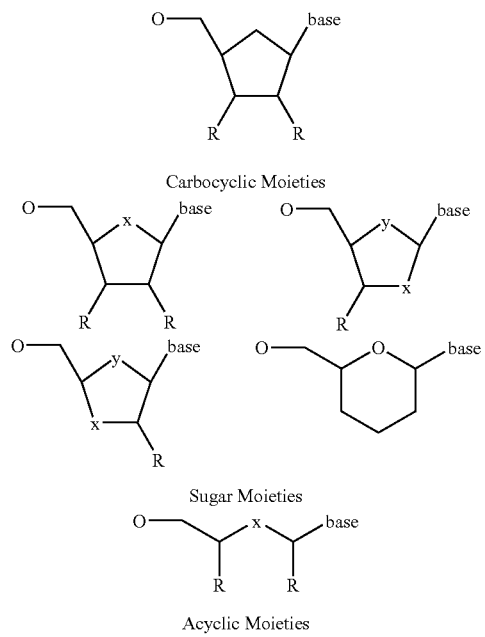

Carbocyclic Moieties

Sugar Moieties

Acyclic Moieties

In certain embodiments, the sugar moiety may be selected from the following: ribosyl, 2'-deoxyribosyl, 3'-deoxyribosyl, 2', 3'-dideoxyribosyl, 2',3'-didehydrodideoxyribosyl, 2'-alkoxyribosyl, 2'-azidoribosyl, 2'-aminoribosyl, 2'-fluororibosyl, 2'mercaptoriboxyl, 2'-alkylthioribosyl, 3'-alkoxyribosyl, 3'-azidoribosyl, 3'-aminoribosyl, 3'-fluororibosyl, 3'mercaptoriboxyl, 3'-alkylthioribosyl, carbocyclic, acyclic and other modified sugars.

Moreover, in Formula I above, the base may include uracil, thymine, cytosine, 5-methylcytosine, guanine, 7-deazaguanine, hypoxanthine, 7-deazahypoxanthine, adenine, 7-deazaadenine, 2,6-diaminopurine or analogs thereof.

The enzyme-activatable label attached at the terminal phosphate position of the nucleotide may be selected from 1,2-dioxetane chemiluminescent compounds, fluorogenic dyes, chromogenic dyes, mass tags, electrochemical tags or combinations thereof. This would allow the detectable species to be detectable by the presence of any one of color, fluorescence emission, chemiluminescence, or a combination thereof.

The enzyme-activatable label may also be a chemical moiety that becomes a substrate for an additional chemical or enzymatic reaction that results in the production of a detectable signal.

Wherein the phosphorylated label shown in Formula I above is a fluorogenic moiety, it is desirably selected from one of the following examples (shown as their phosphate esters): 2-(5'-chloro-2'-phosphoryloxyphenyl)-6-chloro-4-(3H)-quinazolinone, sold under the trade name ELF 97 (Molecular Probes, Inc.), fluorescein diphosphate, fluorescein 3'(6')-O-alkyl-6'(3')-phosphate, 9H-(1,3-dichloro-9,9-dimethylacridin-2-one-7-yl)phosphate, 4-methylumbelliferyl phosphate, resorufin phosphate, 4-trifluoromethylumbelliferyl phosphate, umbelliferyl phosphate, 3-cyanoumbelliferyl phosphate, 9,9-dimethylacridin-2-one-7-yl phosphate, and 6,8-difluoro-4-methylumbelliferyl phosphate. Structures of these dyes are shown below:

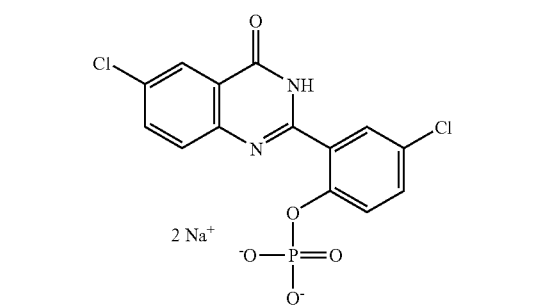

2-(5'-chloro-2'-phosphoryloxyphenyl)-6-chloro-4-(3H)-quinazolinone

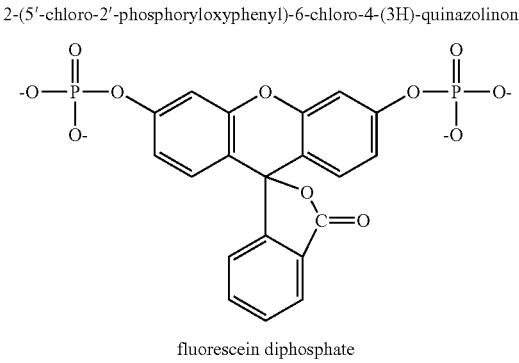

fluorescein diphosphate

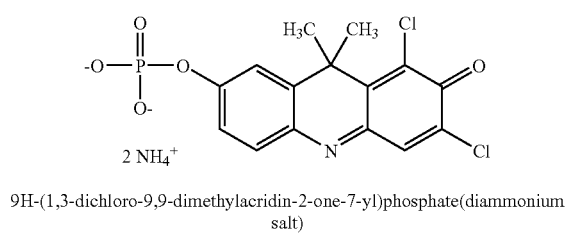

flourescein 3'(6')-O-alkyl-6'(3')-phosphate

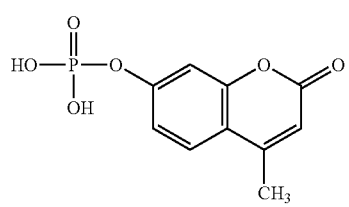

9H-(1,3-dichloro-9,9-dimethylacridin-2-one-7-yl)phosphate(diammonium salt)

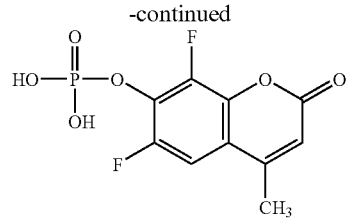

4-methylumbelliferyl phosphate

-continued

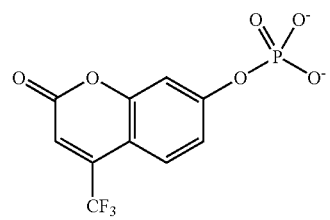

6,8-difluoro-4-methylumbelliferyl phosphate

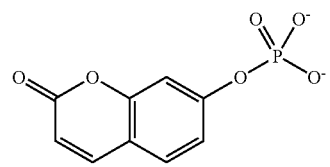

4-Trifluoromethylumbelliferyl phosphate

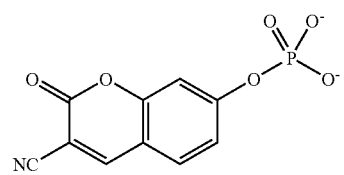

Umbelliferyl phosphate

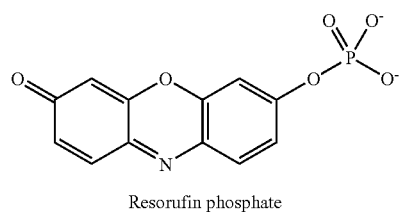

3-Cyanoumbelliferyl phosphate

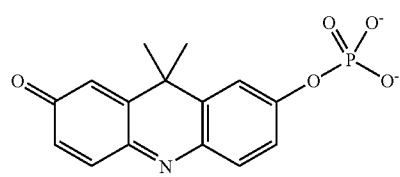

Resorufin phosphate 9,9-dimethylacridin-2-one-7-yl phosphate

Wherein the phosphorylated label shown in Formula I above is a chromogenic moiety, it may be selected from the following moieties (shown as the phosphate esters): 5-bromo-4-chloro-3-indolyl phosphate, 3-indolyl phosphate, p-nitrophenyl phosphate and derivatives thereof. The structures of these chromogenic dyes are shown below:

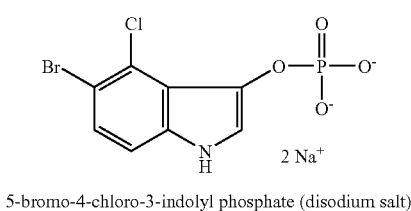

5-bromo-4-chloro-3-indolyl phosphate (disodium salt)

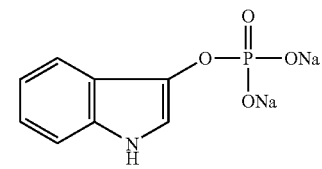

3-indolyl phosphate (disodium salt)

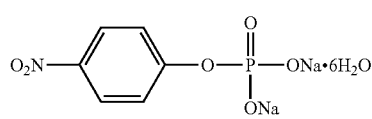

p-nitrophenyl phosphate

The moiety at the terminal phosphate position may further be a chemiluminescent compound wherein it is desired that it is an alkaline phosphatase-activated 1,2-dioxetane compound. The phosphate esters of the 1,2-dioxetane compound may include, but are not limited to, disodium 2-chloro-5-(4-methoxyspiro[1,2-dioxetane-3,2'-(5-chloro-)tricyclo[3,3,1-1$^{3,7}$]-decan]-1-yl)-1-phenyl phosphate, sold under the trade name CDP-Star (Tropix, Inc., Bedford, Mass.), chloroadamant-2'-ylidenemethoxyphenoxy phosphorylated dioxetane, sold under the trade name CSPD (Tropix), and 3-(2'-spiroadamantane)-4-methoxy-4-(3''-phosphoryloxy)phenyl-1,2dioxetane, sold under the trade name AMPPD (Tropix). The structures of these commercially available dioxetane compounds are disclosed in U.S. Pat. Nos. 5,582,980, 5,112,960 and 4,978,614, respectively, and are shown below:

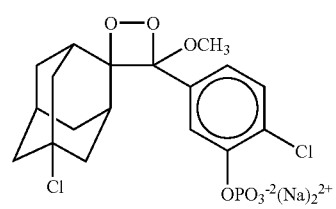

disodium 2-chloro-5-(4-methoxyspiro[1,2-dioxetane-3,2'-(5-chloro-)tricyclo[3,3,1-1$^{3,7}$]-decan]-1-yl)-phenyl phosphate

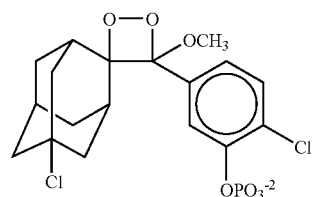

chloroadamant-2'-ylidenemethoxyphenoxy phosphorylated dioxetane

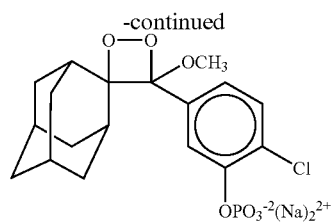

3-(2'-spiroadamantane)-4-methoxy-4-(3''-phosphoryloxy) phenyl-1,2-dioxetane

In certain methods of the present invention, a non-hydrolyzable primer is required. With these methods, a 3'-5' exonuclease is present which could potentially remove the 3'-nucleotide from the primer, eliminating the specificity of the primer. Such hydrolysis can be blocked by the use of non-hydrolyzable linkages between the 3'-end and penultimate nucleotides. As described above, the 3'→5' exonuclease activity may be associated with the DNA polymerase itself. Suitable DNA polymerases for use in the present invention include, but are not limited to, the Klenow fragment of DNA polymerase I, Phi 29 DNA polymerase, DNA polymerase I, T4 DNA polymerase Thermo Sequenase (Amersham Biosciences Corporation), Amplitaq FS (Applied Biosystems), reverse transcriptase, and T7 DNA polymerase.

Methods for synthesizing nuclease-resistant oligonucleotide primers are not particularly limited, and any suitable method known in the art may be used. For example, in one embodiment of the method provided by the invention, the non-hydrolyzable primer is phosphorothioated at the 3'-most phosphodiester linkage terminal. Methods of chemically synthesizing an oligonucleotide primer having nuclease resistance by introducing a phosphorothioate bond into the target site of the primer are well known. In one method, the primer may be chemically synthesized using a modified phosphoramidite method in which the usual oxidation step by iodine water is replaced with an oxidation treatment with a reagent suitable for phosphorothioation, such that a phosphorothioate bond may be introduced in place of the usual phosphodiester bond. One suitable reagent for phosphorothioation is Beaucage's Reagent (3H-1,2-benzodithiole-3-one 1,1-dioxide). This method can be used to introduce a phosphorothioate bond into the primer at any chosen site, including at the 3'-most phosphodiester linkage.

In any event, the presence of a phosphorothioate bond in place of a phosphodiester bond in the vicinity of the 3'-terminal of the oligonucleotide primer confers a resistance on the part of the primer to an exonuclease cleaving from the 3'-terminal side. The oligonucleotide primer is sufficiently non-hydrolyzable by the introduction of only a single phosphorothioate bond.

Reaction conditions such as buffer, pH, and temperature should be selected to achieve sufficient hybridization, polymerase, nuclease, and phosphatase activities. Temperatures suitable for hybridization depend on the homology between the oligonucleotide primer and the target sequence, but are expected to be in the range of about 20° to about 60° C. The pH values are desired to be in the range of about 7 to 9 in a suitable buffer such as Tris-HCl buffer.

As indicated in the examples below, a target nucleic acid sample must first be denatured by heating at >90° C. for about 5 minutes in a buffered solution containing primer and magnesium, followed by hybridization at a suitable temperature for a sufficient period of time, usually about 10 minutes. The hybridization step may be immediately followed by enzymatic treatment at 20-70° C. with DNA polymerase, a 3'→5' exonuclease if desired, which may be associated with a suitable DNA polymerase, and phosphatase in the presence of corresponding substrates.

The present invention is characterized in that following the hybridization step, at least one terminal-phosphate-labeled deoxynucleoside polyphosphate, DNA polymerase, and phosphatase are added to the system so that a series of nucleotides sequentially located next to the 3'-terminal of the primer and complimentary to the target nucleic acid are incorporated if the 3'-terminal base is base-paired with the corresponding template base, followed by detection of a detectable species which acts as the signal from the target nucleic acid.

It may be helpful to illustrate embodiments of this invention where an unmodified primer is present and separately, where a non-hydrolyzable primer and an exonuclease are present.

The primer becomes hybridized to the target nucleic acid with its 3' end opposite the specific base being tested for. We can consider by way of example a target sequence in which a base with an asterisk above it represents the polymorphism.

```
            *
5'AGTTGCTCTAGCAACCATC3'    or      (SEQ ID NO: 1)

*
5'AGTTGCTCTAGTAACCATC3'            (SEQ ID NO: 2)
```

The primer has the following sequence:

```
     3'GTTGGTAG5'          (SEQ ID NO: 3)
```

A hybrid can be formed as follows:

```
         *                              *
5'AGTTGCTCTAGCAACCATC3'       5'AGTTGCTCTAGTAACCATC3'
      3'GTTGGTAG5'                       TTGGTAG5'
                                        /
                                      3'·G
```

In one format, terminal-phosphate-labeled deoxynucleoside polyphosphates are used in the DNA polymerase reaction step of the methods of this invention and will be incorporated in one case, but not the other as shown below, where the incorporated nucleotides are underlined (SEQ ID NO: 4: 5'-GATGGTTGCTAG-3'):

```
         *                              *
5'AGTTGCTCTAGCAACCATC3'       5'AGTTGCTCTAGTAACCATC3'
      3'GATCGTTGGTAG5'                   TTGGTAG5'
                                        /
                                      3'·G
```

Therefore, C may be identified during analysis by the presence of a detectable species formed following phosphatase digestion of the labeled polyphosphate by-product that is concomitantly formed during incorporation of the phosphatase-resistant nucleotide analog. In order to identify the T in the target sequence, a different primer with same sequence except an A at the 3'-end instead of a G may be used in a separate analysis for production of a detectable species. As shown in the above example, addition of multiple nucleotides to generate multiple molecules of labeled polyphosphate effects the amplification of the signal. Further amplification may be achieved by thermal cycling. Thus after extension of the primer, the sample may be heated to separate the two DNA strands and then cooled to anneal another primer to the target, which can then be extended to generate more signal.

Figure 6:
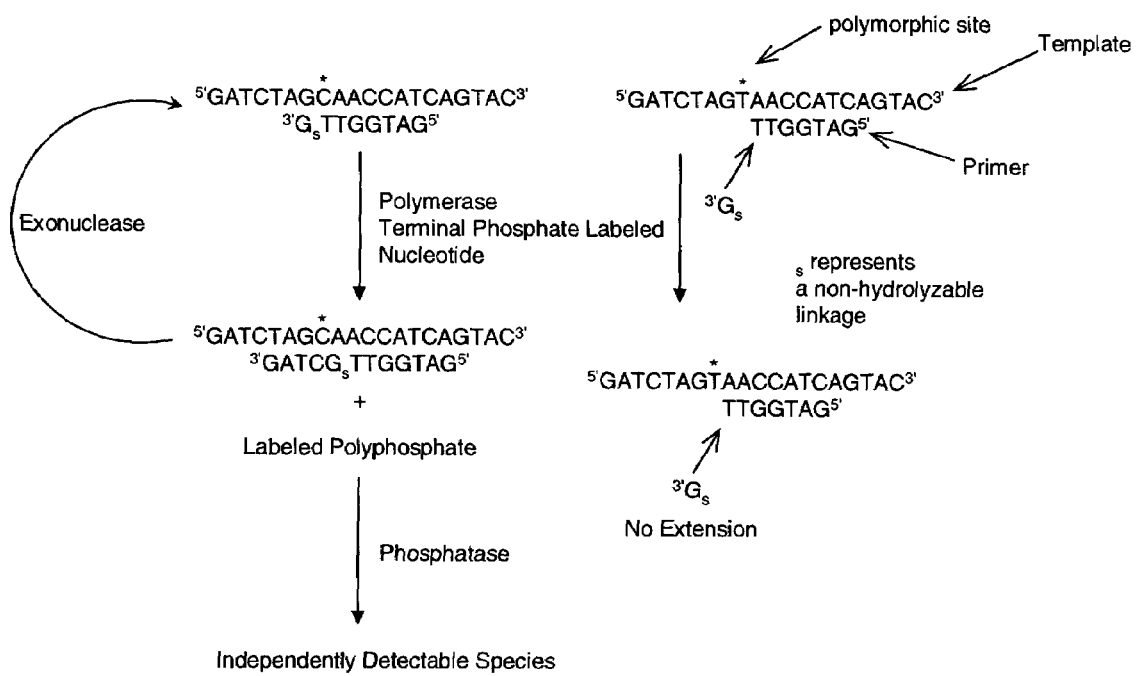
FIG. 6 provides a method for the characterization of a nucleic acid sequence, using a primer with a non-hydrolizable linkage between 3'-terminal nucleotide and the penultimate nucleotide. In this scheme, 5'-GATCTAGCAACCATCAG-TAC-3' is SEQ ID NO: 5; 5'-GATCTAGTAACCATCAG-TAC-3' is SEQ ID NO: 6; 5'-GATGGTTGs-3' is SEQ ID NO: 7 and 5'-GATGGTTGsCTAG-3' is SEQ ID NO: 8.

An alternate format provides a different means of amplifying the signal under isothermal conditions. In this case the primer used has a non-hydrolizable linkage between 3'-terminal nucleotide and the penultimate nucleotide (FIG. 6). The extension is carried out with a polymerase, which adds one or more nucleotides and after extension (partial or complete), a double stranded 3'-exonuclease cleaves the newly added nucleotides to regenerate the original primer template. It is preferable to use a processive polymerase that adds several nucleotides per binding event. In this format, primer selection has to be such that the 3'-end of template remains single stranded, hence, is not a substrate for double stranded 3'-exonuclease. There are other means of protecting template that are known in the art, such as TdT catalyzed 3'-capping with a nuclease resistant nucleotide.

In the scheme above, 5'-GATCTAGCAACCATCAGTAC-3' is SEQ ID NO: 5; 5'-GATCTAGTAACCATCAGTAC-3' is SEQ ID NO: 6; 5'-GATGGTTGs-3' is SEQ ID NO: 7 and 5'-GATGGTTGsCTAG-3' is SEQ ID NO: 8.

EXAMPLES

The following examples illustrate certain preferred embodiments of the illustration that are not intended to be illustrative of all embodiments.

Example 1

Preparation of δ-9H(1,3-dichloro-9,9-dimethylacridin-2-one-7-yl)-thymidine-5'-tetraphosphate (dT4P-DDAO) and other dye-linked tetraphosphates 10 μmoles TTP TEA salt was evaporated to dryness. To the residue was added 40 μmoles tributylamine and 5 ml dry pyridine. The solution was re-evaporated to dryness. After 2 coevaporations with 3 ml dry dimethylformamide (DMF), residue was re-dissolved in 200 μl dry DMF, flushed with argon and stoppered. Using a syringe, 50 μmoles (8 mg) carbonyldiimidazole (CDI) dissolved in 100 μl dry DMF was added. The flask was stirred for 4 hr at ambient temperature.

While the above reaction was progressing, 35 mg (83 μmoles) DDAO phosphate and 166 μmoles tributylamine were dissolved in dry DMF. The DDAO phosphate was evaporated to dryness followed by 3 coevaporations with dry DMF. Residue was dissolved in 300 μl dry DMF.

After the 4 hr reaction time, 3.2 μl anhydrous methanol was added to the TTP-CDI reaction. The reaction was stirred 30 minutes. To this mixture, DDAO phosphate solution was added and mixture was stirred at ambient temperature for 18 hr. The reaction was checked by Reverse phase HPLC (Xterra 4.6×100 column, 0.1M TEAA/ acetonitrile). The reaction volume was reduced to 200 μl by evaporation and the reaction was allowed to progress for 80 hr.

After 80 hr, the reaction was stopped by adding 15 ml 0.1 M TEAB. The diluted mixture was applied to a 19×100 Xterra RP column and eluted with an acetonitrile gradient in 0.1M TEAB. The fractions containing pure dT4P-DDAO were evaporated to dryness and coevaporated twice with ethanol.

The residue was reconstituted with MilliQ water. Yield: 1.10 μmole, 11%; HPLC purity >98% at 455 nm; MS: M−1=850.07 (calc. 849.95)

δ-9H(1,3-dichloro-9,9-dimethylacridin-2-one-7-yl)-deoxyguanosine-5'-tetraphosphate (dG4P-DDAO), δ-9H(1,3-dichloro-9,9-dimethylacridin-2-one-7-yl)-deoxycytidine-5'-tetraphosphate (dC4P-DDAO) and δ-9H(1,3-dichloro-9,9-dimethylacridin-2-one-7-yl)-deoxyadenosine-5'-tetraphosphate (dA4P-DDAO) were prepared in a similar manner as described above except 3.5 equivalents of DDAO phosphate was used instead of 8.3 equivalents. After C18 purification, samples were purified on ion exchange using a Mono Q 10/10 column.

δ-9H(1,3-dichloro-9,9-dimethylacridin-2-one-7-yl)-deoxyguanosine-5'-tetraphosphate (dG4P-DDAO): Yield 0.57 umol, 5.7%; HPLC purity 99% at 455 nm; MS: M−1=875.03 (calc. 874.96).

δ-9H(1,3-dichloro-9,9-dimethylacridin-2-one-7-yl)-deoxycytidine-5'-tetraphosphate (dC4P-DDAO): Yield 0.24umole, 2.4%; HPLC purity 99% at 455 nm; MS: M−1=835.03 (calc. 834.95).

δ-9H(1,3-dichloro-9,9-dimethylacridin-2-one-7-yl)-deoxyadenosine-5'-tetraphosphate (dA4P-DDAO): Yield 0.38 umole, 3.8%; HPLC purity 99% at 455 nm; MS: M−1=859.07 (calc. 858.97).

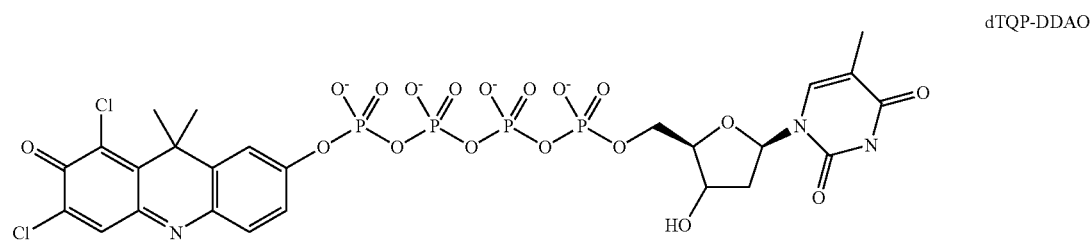

dTQP-DDAO

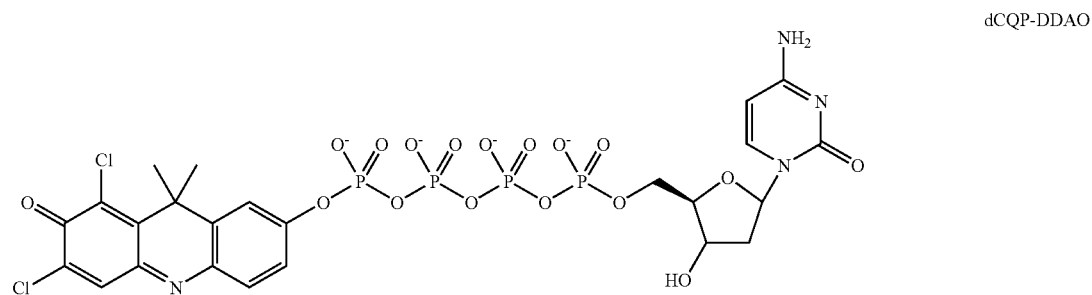

dCQP-DDAO

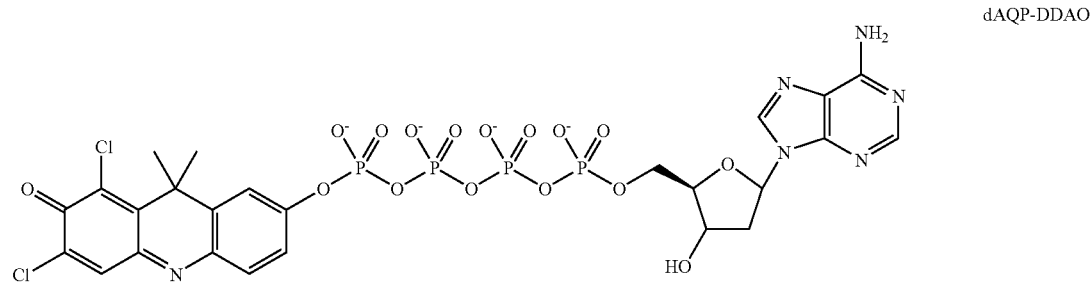

dAQP-DDAO

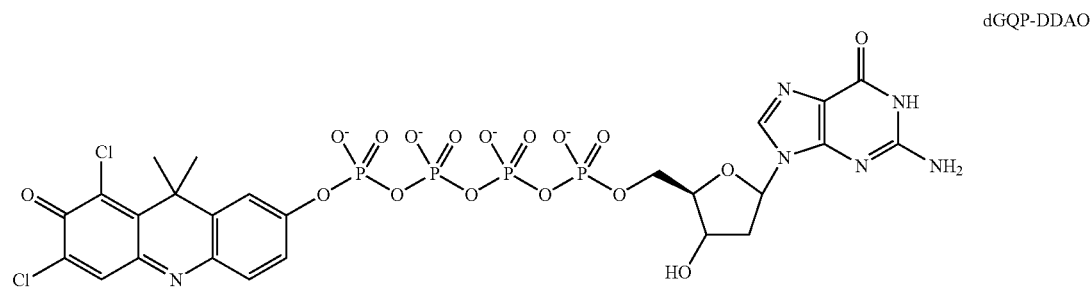

dGQP-DDAO

The synthesis of other terminal phosphate labeled nucleoside polyphosphates was carried out essentially the same way as for the synthesis of DDAO-linked tetraphosphates above. The other dye-linked tetraphosphates synthesized are with the following dyes: methyl coumarin, resorufin, and ethyl fluorescein.

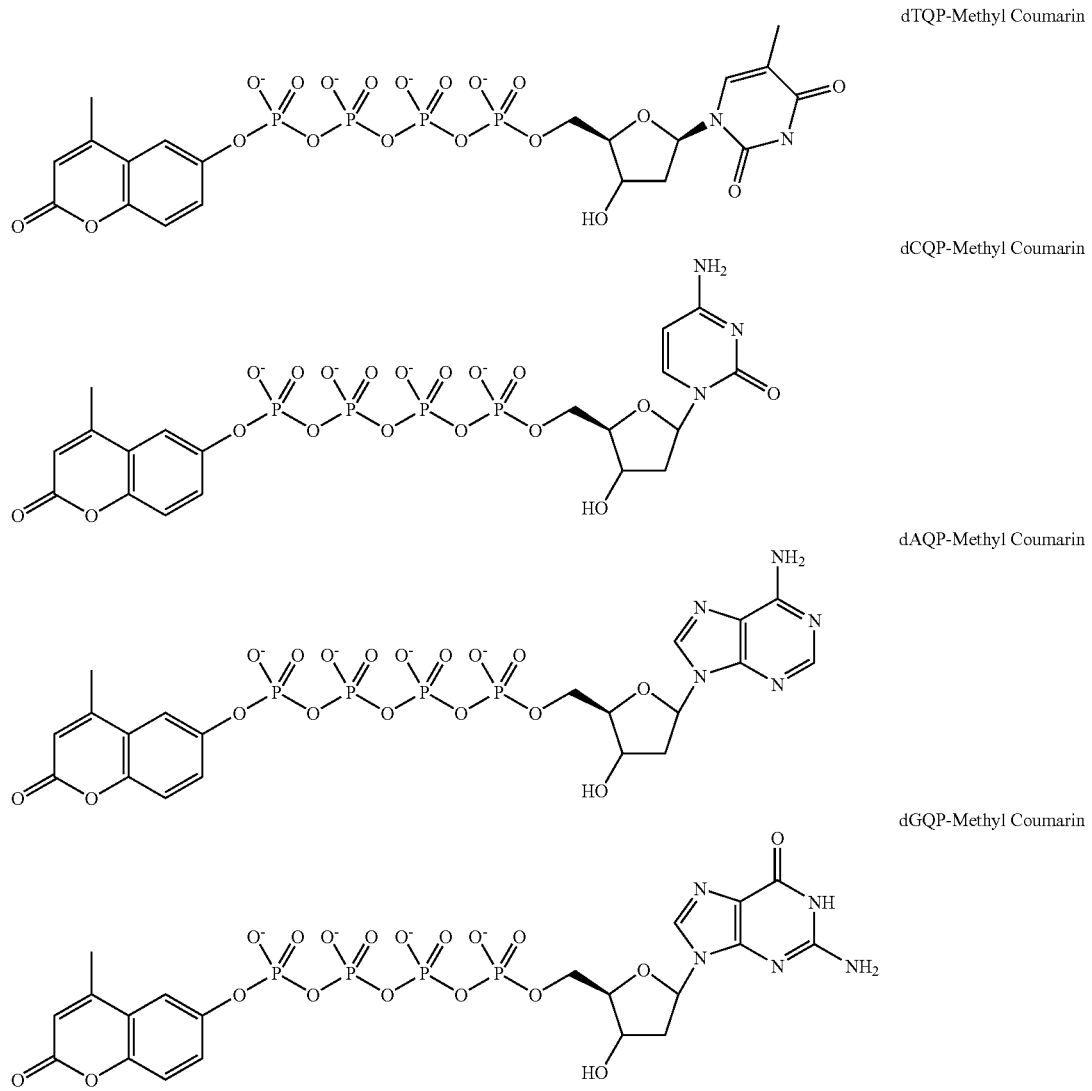

dTQP-Methyl Coumarin dCQP-Methyl Coumarin dAQP-Methyl Coumarin dGQP-Methyl Coumarin Example 2

Discrimination of Alleles Using an Allele Specific Primer and Terminal Phosphate Labeled Nucleoside Polyphosphates The following primers and templates were used in Examples 2, 3 and 4.

```
Primers:
5'-GTT CTC GGC ATC ACC ATC CG(s)T-3'         (SEQ ID NO: 9)

5'-GTT CTC GGC ATC ACC ATG CG(s)T-3'         (SEQ ID NO: 10)

5'-GTT CTC GGC ATC ACC ATC GG(s)T-3'         (SEQ ID NO: 11)
```

-continued

```
Templates:
5'-CAC CCT TAT CTG GTT GTC GAC GGA TGG TGA TGC CGA GAA C-3'  (#1, SEQ ID NO: 12)

5'-CAC CCT TAT CTG GTT GTC GGC GGA TGG TGA TGC CGA GAA C-3'  (#2, SEQ ID NO: 13)

5'-CAC CCT TAT CTG GTT GTC GCC GGA TGG TGA TGC CGA GAA C-3'  (#3, SEQ ID NO: 14)

5'-CAC CCT TAT CTG GTT GTC GTC GGA TGG TGA TGC CGA GAA C-3'  (#4, SEQ ID NO: 15)
```

Reactions were assembled at room temperature (23° C.) using the deoxynucleotides of Example (1). Reactions contained primer template combinations having a single oligonucleotide primer (represented by SEQ ID NO: 9) annealed to one of two different oligonucleotide templates with either a dA or a dG at the polymorphic site opposite to the 3' terminal nucleotide of the primer, corresponding to Template #1 and Template #2, respectively.

Figure 3:
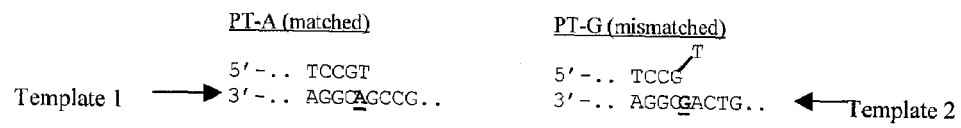
FIG. 3 is a graph of time versus fluorescence emission obtained by the use of a phosphatase to generate signal after incorporation of nucleotides labeled on the terminal phosphate with fluorogenic dyes by a DNA polymerase, Sequenase. Matched primers shows rapid rise in fluorescence and a very high signal compared to mismatched primer.
Figure 3:
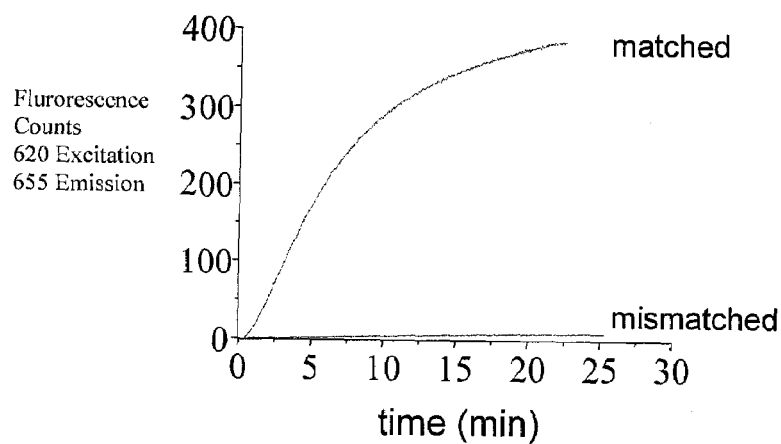

Referring now to FIG. 3, for template #1 in the present example, DNA polymerase would be expected to extend the primer with labeled dNTP's, while for template #2 in FIG. 3, DNA polymerase wouldn't be expected to extend the primer.

Reaction conditions: A 70 µl reaction containing 25 mM Tris, pH 8.0, 50 mM NaCl, 0.125 mM $MgCl_2$, 0.5 mM $MnCl_2$, 0.01% tween-20, 0.25 units shrimp alkaline phosphatase, 50 nM primer annealed to template, and 1 µM each dNTP-DDAO was assembled in a quartz fluorescence ultra-microcuvet in a LS-55 Luminescence Spectrometer (Perkin Elmer), operated in time drive mode. Excitation and emission wavelengths are 620 nm and 655 nm respectively. Slit widths were 5 nm for excitation slits, 15 nm for emission slits. The reaction was initiated by the addition of 9 units of DNA polymerase, Sequenase.

As shown in FIG. 3, dye emission was detected only with Primer: Template 1, where the 3'-terminal base of the primer was base paired with corresponding template base. Cleavage of the pyrophosphate product of phosphoryl transfer by shrimp alkaline phosphatase leads to a detectable change in the DDAO label which allows for the detection of the nucleic acid. No detectable dye emission was obtained with Primer: Template 2.

Example 3

Figure 7:
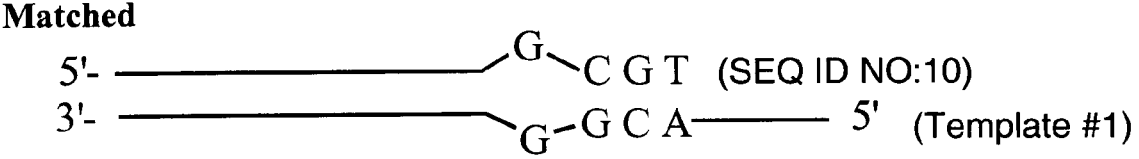
FIG. 7 is a schematic drawing showing the annealed primer/template pairs as used in Example 3 of the current invention.
Figure 7:
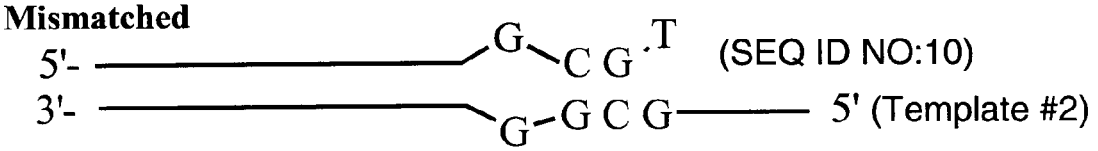

Discrimination of Alleles Using an Allele Specific Primer and Terminal Phosphate Labeled Nucleoside Polyphosphates: Effect of Internal Mismatches For FIG. 4a, primer with a sequence of SEQ ID NO: 9 and template #1 or template #2 with correct or incorrect base at 3'-end was used. For FIG. 4b, primer with a sequence of SEQ ID NO: 10 with internal mismatch three bases away from the 3'-end and template #1 or template #2 with correct or incorrect base at 3'-end was used. FIG. 7 is a schematic drawing showing the annealed primer/template pairs as used in Example 3 of the current invention.

Figure 4:
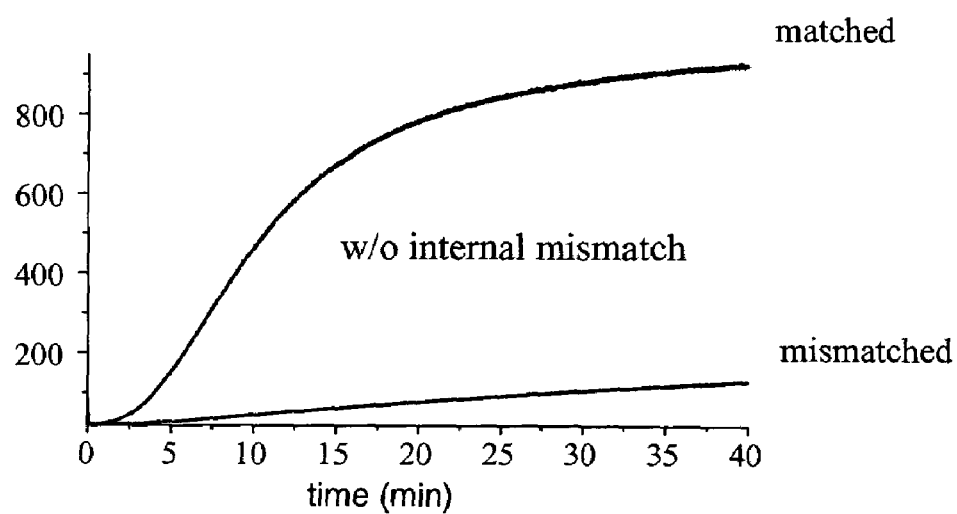
FIG. 4 is a graph of time versus fluorescence emission obtained by the use of a phosphatase to generate signal after incorporation of nucleotides labeled on the terminal phosphate with fluorogenic dyes by a DNA polymerase, Sequenase. Matched primer shows rapid rise in fluorescence and a very high signal compared to mismatched primer.
Figure 4:
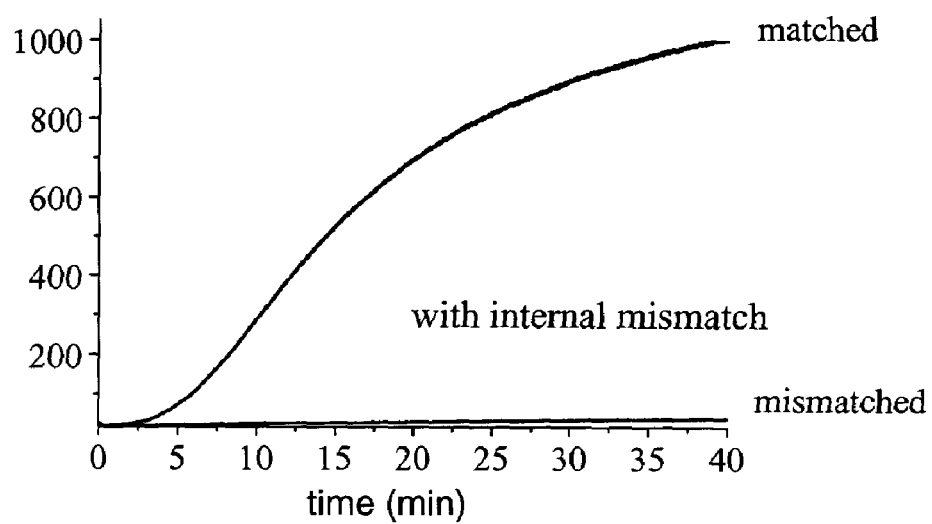

The experiment was carried out essentially in the same manner as reported above in example 2. The results are shown in FIG. 4. It is clear that the internal mismatch enhance the signal to background ratio by approximately ten folds.

Example 4

Discrimination of Alleles Using an Allele Specific Primer and Terminal Phosphate Labeled Nucleoside Polyphosphates Using Phi 29 DNA Polymerase The experiments reported in examples 2 and 3 with correct or incorrect base at the 3'-end of the primer as well as with internal mismatch were repeated using Phi 29 D12A DNA polymerase in place of Sequenase.

Figure 5:
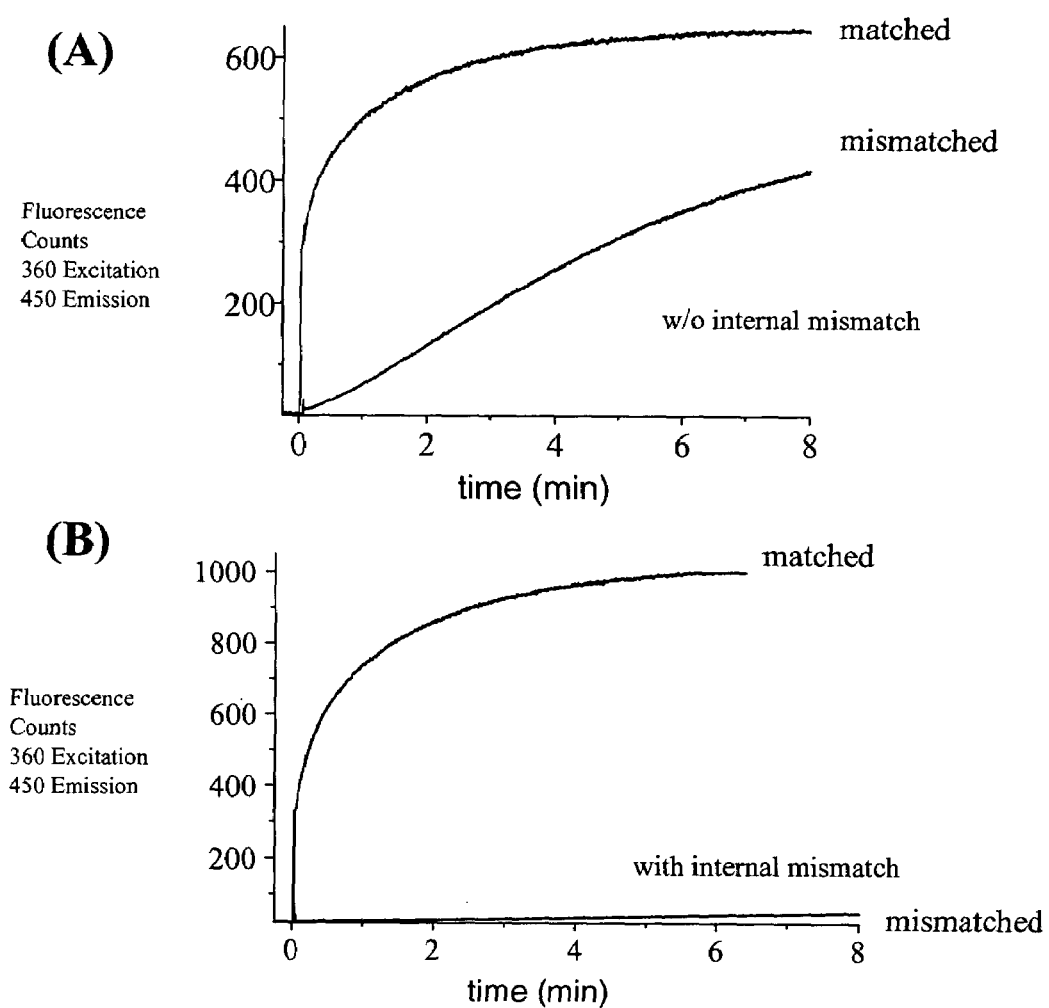
FIG. 5 is a graph of time versus fluorescence emission obtained by the use of a phosphatase to generate signal after incorporation of nucleotides labeled on the terminal phosphate with fluorogenic dyes by a Phi 29 D12A DNA polymerase. Matched primer with internal mismatch shows rapid rise in fluorescence and a very high signal compared to mismatched primer.

Compared to Sequenase, Phi 29 D12A DNA polymerase is less discriminatory between the terminal match and mismatch, but presence of an internal mismatch enhances the discriminatory capability of Phi 29 DNA polymerase (FIG. 5).

Having described the particular, desired embodiments of the invention herein, it should be appreciated that modifications may be made there through without departing from the contemplated scope of the invention. The true scope of the invention is set forth in the claims appended hereto.

What is claimed is:

1. A method of detecting a polymorphic site of a nucleic acid template comprising the steps of:
   (a) conducting a nucleic acid polymerase reaction in a solution comprising a nucleic acid template which contains a polymorphic site, an allele specific primer whose 3' terminal base is complementary to the nucleotide of the polymorphic site of said nucleic acid template, two or more terminal phosphate-labeled nucleotides which are non-reactive to phosphatases, and a DNA polymerase so that a labeled polyphosphate is produced;
   (b) mixing a phosphatase with said solution in step (a) and producing a labeled detectable species from said labeled polyphosphate;
   (c) detecting said labeled detectable species wherein the detection of said labeled detectable species indicates the presence of the polymorphic site in said nucleic acid template.

2. The method of claim 1, wherein the steps (a) and (b) are carried out simultaneously.

3. The method of claim 1, wherein the label in said terminal phosphate-labeled nucleotides is selected from the group consisting of an electrochemical label, a mass tag, a chromogenic dye label, chemiluminescent dye label, and fluorescent dye label.

4. The method of claim 1, wherein said allele specific primer is nuclease resistant and said conducting step further includes an enzyme having 3'→5' exonuclease activity.

5. The method of claim 4, wherein said nuclease resistant primer has a methyl phosphonate, a borano phosphate or a phosphorothioate linkage at the 3' end of the primer.

6. The method of claim 1 further comprising adding one or more additional detection reagents in said conducting step, and said additional detection reagents are different from said labeled polyphosphate.

7. The method of claim 1, wherein said allele specific primer has a mismatch located at one, two or three bases away from the 3'-end base of said allele specific primer.

8. The method of claim 1, wherein the polyphosphate chain of at least one of said terminal phosphate-labeled nucleotides comprises four, five or six phosphate groups.

9. The method of claim 1 wherein, said DNA polymerase is selected from the group consisting of the Klenow fragment of DNA polymerase I, Phi 29 DNA polymerase, DNA polymerase I, T4 DNA polymerase, Thermo Sequenase, Sequenase, Taq DNA polymerase, pfu DNA polymerase, Amplitaq FS, reverse transcriptase and T7 DNA polymerase.

10. The method of claim 1, wherein said DNA polymerase has 3'→5' exonuclease activity and said allele specific primer is nuclease resistant.

11. The method of claim 1, wherein each of said two or more terminal phosphate-labeled nucleotides is:

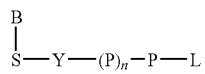

wherein P is phosphate ($PO_3$); n is 2 to 4; Y is an oxygen or sulfur atom; B is a purine, deazapurine, or pyrimidine base; S is an acyclic moiety, carbocyclic moiety or sugar moiety; and L is an enzyme-activatable label containing a hydroxyl group, a sulfhydryl group or an amino group suitable for forming a phosphate ester, a thioester or a phosphoramidate linkage at the terminal phosphate of a natural or modified nucleotide.

12. The method of claim 11, wherein said sugar moiety is selected from the group consisting of ribosyl, 2'-deoxyribosyl, 3'-deoxyribosyl, 2',3'-dideoxyribosyl, 2',3'-didehydrodideoxyribosyl, 2'-alkoxyribosyl, 2'-azidoribosyl, 2'-aminoribosyl, 2'-fluororibosyl, 2'-mercaptoriboxyl, 2'-alkylthioribosyl, 3'-alkoxyribosyl, 3'-azidoribosyl, 3'-aminoribosyl, 3'-fluororibosyl, 3'-mercaptoriboxyl, 3'-alkylthioribosyl, carbocyclic, acyclic and other modified sugars.

13. The method of claim 11, wherein said base is selected from the group consisting of uracil, thymine, cytosine, guanine, 7-deazaguanine, hypoxanthine, 7-deazahypoxanthine, adenine, 7-deazaadenine, 2,6-diaminopurine and analogs thereof.

14. The method of claim 11, wherein said enzyme-activatable label is selected from the group consisting of chemiluminescent compounds, fluorogenic dyes, chromogenic dyes, and electrochemical tags.

15. The method of claim 14, wherein said chromogenic dyes are selected from the group consisting of 5-bromo-4-chloro-3-indolyl phosphate, 3-indoxyl phosphate, p-nitrophenyl phosphate, and derivatives thereof.

16. The method of claim 11, wherein said P-L in said terminal phosphate-labeled nucleotides is a phosphorylated label comprising a fluorogenic dye selected from the group consisting of 2-(5'-chloro-2'-phosphoryloxyphenyl)-6-chloro-4-(3H)-quinazolinone, fluorescein diphosphate, fluorescein 3'(6')-O-alkyl-6'(3')-phosphate, 9H-(1,3-dichloro-9,9-dimethylacridin-2-one-7-yl)phosphate, 4-methylumbelliferyl phosphate, resorufin phosphate, 4-trifluoromethylumbelliferyl phosphate, umbelliferyl phosphate, 3-cyanoumbelliferyl phosphate, 9,9-dimethylacirdin-2-one-7-yl phosphate, 6,8-difluoro-4-methylumbelliferyl phosphate, and derivatives thereof.

17. The method of claim 14, wherein said chemiluminescent compounds are alkaline phosphatase-activated 1,2-dioxetane compounds.

18. The method of claim 17, wherein said 1,2-dioxetane compounds are selected from the group consisting of 2-chloro-5-(4-methoxyspiro[1,2-dioxetane-3,2'-(5-chloro-)tricyclo[3,3,1-13,7]-decan]-1-yl)-1-phenyl phosphate, chloroadamant-2'-ylidenemethoxyphenoxy phosphorylated dioxetane, 3-(2'-spiroadamantane)-4-methoxy-4-(3"-phosphoryloxy)phenyl-1,2-dioxetane and derivatives thereof.

19. The method of claim 1, wherein said nucleic acid polymerase reaction are performed for multiple cycles.

* * * * *